United States Patent [19]
Watts

[11] Patent Number: 4,676,777
[45] Date of Patent: Jun. 30, 1987

[54] IRRIGATION-EVACUATOR SURGICAL IMPLEMENT WITH DISPLACEABLE VALVE

[76] Inventor: George T. Watts, 4, Amesbury Road, Moseley, Birmingham B13 8LD, England

[21] Appl. No.: 588,142

[22] Filed: Mar. 9, 1984

[30] Foreign Application Priority Data

Mar. 17, 1983 [GB] United Kingdom ............ 8307449

[51] Int. Cl.$^4$ ............................................ A61M 1/00
[52] U.S. Cl. ...................................... 604/33; 604/37; 604/249
[58] Field of Search ............... 137/102; 222/207, 212; 604/33, 185, 212, 217, 316, 249, 73–75, 36–38, 183

[56] References Cited

U.S. PATENT DOCUMENTS

| 1,015,895 | 1/1912 | Kelley | 604/37 |
| 3,003,500 | 10/1961 | Barton et al. | 604/185 |
| 3,516,443 | 6/1970 | Hughes | 137/102 |
| 3,519,012 | 7/1970 | Van Patten | 137/102 |
| 3,780,736 | 12/1973 | Chen | 604/37 |
| 3,892,226 | 7/1975 | Rosen | 604/37 |
| 4,038,983 | 8/1977 | Mittleman et al. | 604/185 |

FOREIGN PATENT DOCUMENTS 311726 1/1918 Fed. Rep. of Germany .

Primary Examiner—J. L. Kruter
Attorney, Agent, or Firm—Fulwider, Patton, Rieber, Lee & Utecht

[57] ABSTRACT

An implement providing an irrigator/evacuator primarily intended for use in connection with urological surgery, includes a reservoir connected to one side of the barrel of a pump having an outlet opening at one end. A compressible bulb attached to the end of the barrel opposite the outlet opening can be utilized to displace fluid within the implement outwardly through the outlet opening for irrigation purposes, and subsequently to draw fluid into the implement for evacuation purposes. A free piston is housed within the pump so as to freely movable along the length of the barrel. Fluid drawn into the implement causes movement of the piston to a retracted position, allowing substantially unrestricted passage of pieces of tissue or other material into the reservoir. The outward displacement of fluid from the implement, on the other hand, causes movement of the piston toward the outlet end of the barrel, in which position the piston effectively prevents the expulsion of tissue and the like from the implement, without significantly restricting fluid flow.

10 Claims, 1 Drawing Figure

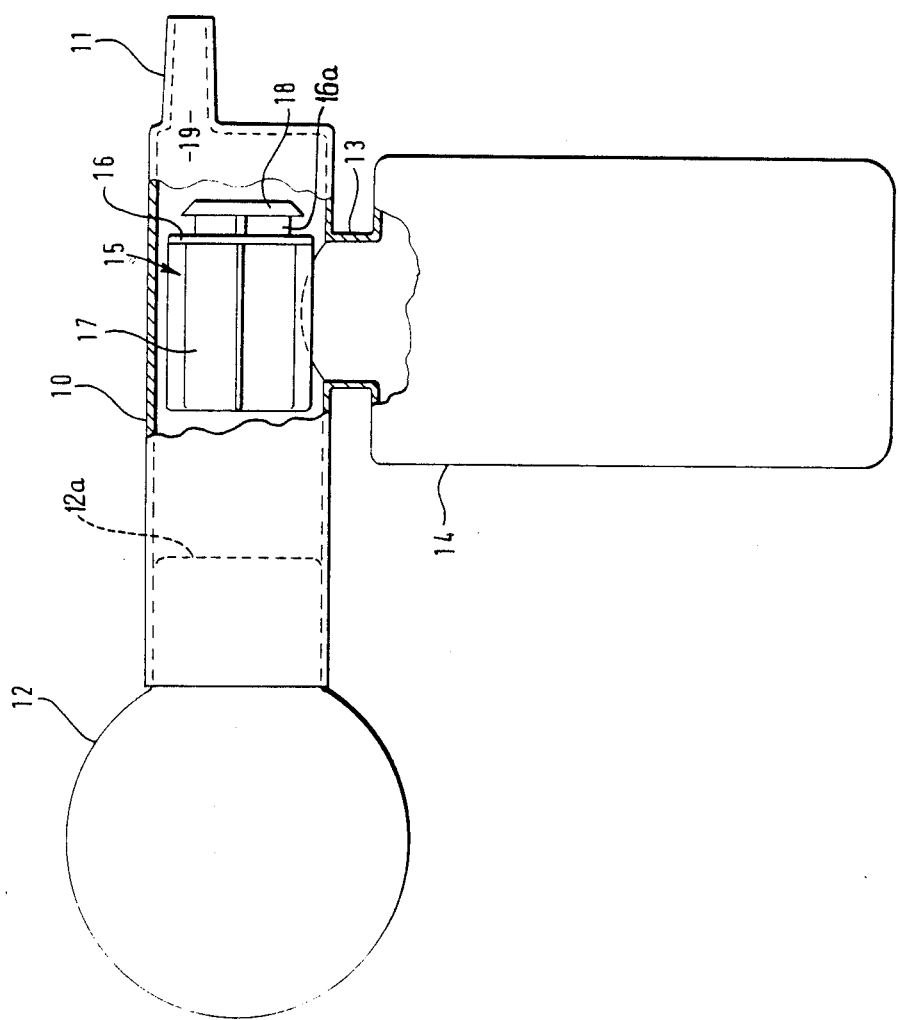

IRRIGATION-EVACUATOR SURGICAL IMPLEMENT WITH DISPLACEABLE VALVE

BACKGROUND TO THE INVENTION

1. Field of the Invention

This invention relates to a surgical implement comprising an irrigator/evacuator primarily but not exclusively intended for use in connection with urological surgery, for example prostatic surgery.

In some surgical operations it is necessary to remove tissue or other fragments from the bladder using a technique which involves repeatedly forcing water or other suitable fluid into the bladder and then extracting such fluid whilst separating entrained tissue or other matter to prevent its being reintroduced.

2. Description of the Prior Art

Implements at present in use for this purpose are quite complicated and costly to manufacture. Consequently, they are used repeatedly and need to be disassembled, cleaned and sterilised for re-use. The object of the invention is primarily to provide an implement of simplified design which works as efficiently as known implements, but can be manufactured sufficiently economically for it to be used only once and then discarded.

SUMMARY OF THE INVENTION

The present invention resides in an implement for the purpose described above, which comprises a reservoir vessel for an irrigation fluid, a double-acting manually operable pump connected to said vessel and having an outlet opening whereby said fluid may be displaced outwardly and withdrawn inwardly through said opening, and in said pump a member which is displaced during outward displacement of said fluid into a position in which it effectively restrains passage of pieces of tissue carried by said fluid in the direction towards said opening whilst allowing substantially unrestricted flow of said fluid, and which is displaceable during inward withdrawal of the fluid into a position in which it allows free passage of said fluid and pieces of tissue in the direction away from said opening.

The pump may comprise a barrel having said opening at one end, with said reservoir vessel connected to the barrel by a side tube a point near the outlet opening. For displacing fluid, a compressible bulb may be provided at the end of the barrel remote from said opening. Alternatively, a manually operable piston may be provided for this purpose.

The displaceable member preferably comprises a free piston loosely received in the barrel so as to move along the barrel in response to fluid flow. In the first said position, said piston may be disposed at least partially between the side tube and said outlet opening so as partially to obstruct said barrel and thereby effectively prevent passage of pieces of tissue towards said opening. Preferably, in the first said position the piston also partially obstructs the mouth of the side tube so as effectively to prevent passage of pieces of tissue outwardly from the side tube. In the second said position the piston may be disposed so that said side tube is at least partially unobstructed and both fluid and pieces of tissue entrained therein may flow without obstruction from said outlet and into to said side tube.

The implement may be made of any suitable plastics material and can conveniently be supplied in a sterilised pack so as to be immediately available for use. Following such use, the implement may then be discarded.

BRIEF DESCRIPTION OF THE DRAWING

The invention will now be described by way of example with reference to the accompanying drawing which illustrates one embodiment.

DESCRIPTION OF THE PREFERRED EMBODIMENTS

As shown, the implement comprises a manually operable pump which includes a tube or barrel 10 having an outlet nozzle 11 at one end thereof, preferably at an eccentric position. The other end of the barrel 10 is closed by means of a conventional compressible bulb 12. A side tube 13 near the nozzle end of the barrel connects with a bottle or reservoir 14. A free piston 15 is located within the barrel 10 and is so dimensioned as to have a significant clearance with respect to the internal wall of the barrel. The piston is conveniently of a known type which includes a transverse disc 16 with several radially arranged flat fins 17 on the side thereof remote from the nozzle 11. Additionally, the disc 16 carries a flat abutment member 18 spaced from the side thereof by a spacer member 16a forming an integral part of the piston 15. The flat abutment member 18 is presented towards the nozzle and of transverse dimensions less than those of the disc 16.

In use, the implement is entirely filled with water or other suitable irrigation fluid. When the bulb 12 is squeezed, water is displaced outwardly through the nozzle 11. The water flow causes the piston 15 to move up to the nozzle end of the barrel 10, and the abutment member 18 maintains a predetermined minimum spacing between the disc 16 and the opening 19 at the mouth of the nozzle, so that the flow of water is effectively unobstructed. Likewise the clearance between the disc 16 and the internal wall of the barrel 10 is such as to allow effectively unrestricted flow of water towards the nozzle 11.

When pressure on the bulb 12 is released, water is drawn back into the barrel through the nozzle 11, and the piston 15 is thereby displaced towards the bulb. The end 12a of the bulb within the tube may serve as an abutment which is engaged by the fins 17 to limit withdrawal of the piston to a position in which the mouth of the side tube is effectively unobstructed without being removed entirely from the mouth. Alternatively, the barrel 10 may be formed with a shoulder or constriction which affords an abutment for this purpose. Water drawn in through the nozzle 11 tends to impinge on the piston 16, and by virtue of the off-centre location of the nozzle, the water tends to swirl downwardly towards the mouth of the side tube 13 leading to the reservoir 14.

The nozzle is so dimensioned as to enable pieces of tissue having a length of typically 2 to 3 centimeters and a thickness of some 2 to 3 millimeters to pass through. Typically, the internal diameter of the nozzle may be about 5 millimeters. Such pieces of tissue tend to pass into the reservoir 14 by virtue of the swirling action described above, together with gravitational separation effects and become trapped there.

On recompression of the bulb 12, water is again displaced outwardly through the nozzle 11 and the piston 15 returns to the nozzle end of the barrel so as to form an effective obstruction to pieces of tissue. The fins 17 and disc 16 of the piston 15, as it is forced across the mouth of the side tube 13, act to obstruct passage out of the reservoir 14 of any pieces of tissue still entrained in the water and when the piston 15 engages the end of the barrel 10, the opening 19 may be partially occluded by the abutment disc 18 so as further to obstruct passage of pieces of tissue back through the nozzle 11, but without substantially restricting water flow.

Since the reservoir 14 has a relatively large volume, pieces of tissue will tend to settle to the bottom of the reservoir. Moreover, since the outward flow of water is predominently across the mouth of the side tube and along the length of the barrel, there is relatively little risk of pieces of tissue being swept upwardly from the reservoir. Consequently, any pieces which remain in, or return to, the barrel are unlikely to be sufficient to obstruct the outward flow of water significantly, because of the substantial clearance around the edge of the disc 16, and yet such disc, particularly in combination with the fins 17 and abutment 18, is effective to obstruct pieces of tissue from returning towards the nozzle 11, should they be present in the barrel.

Instead of employing a bulb 12 as the means for displacing water from the implement, it would alternatively be possible to use an additional, close fitting piston within the barrel 11, in the manner of a syringe. Such additional piston could be entirely separate from the piston 15, which thus would still be a free piston, but alternatively such close fitting piston could be formed integrally with the piston 15, or otherwise rigidly connected thereto so that the two move together.

In a further modification, such a close fitting piston, whether separate from or integral with the piston 15, could be operated by means of a lever or trigger mounted pivotally in a pistol-type hand grip provided at the end of the barrel.

The illustrated embodiment can be manufactured simply and economically as a moulding of plastics material, and can make use of a standard compression bulb 12 and a piston 15 which may also be of standard form, as used in the manufacture of a syringe, for example. It is easy to sterilise and light in weight so that it can be supplied, ready for use, in a sterile pack and then be discarded after use.

Instead of forming the reservoir vessel 14 integrally with the barrel 10 as shown, it would be possible for the side tube to terminate, for example, in a threaded collar adapted to receive releasably a bottle of glass or plastics material having a correspondingly threaded neck. In that case, the bottle may be of any standard size and shape, and may be re-used after sterilisation if required.

I claim:

1. A surgical implement for use as an irrigator/evacuator comprising reservoir means, double-acting manually operable pump means connected to said reservoir means and having a barrel with an outlet opening at one end thereof through which fluid may be displaced outwardly and withdrawn inwardly by the operation of the pump means, and a displaceable piston having a transverse disc and radially arranged fins on a side of the disc remote from the outlet opening arranged within said barrel for movement between a first position adjacent to said outlet opening and a second position spaced inwardly from said opening, the displaceable piston being so dimensioned and shaped as to partially obstruct said outlet opening when in said first position in order to restrain passage of pieces of tissue.

2. A surgical implement as claimed in claim 1 wherein said piston further includes an abutment member spaced from a side of said disc presented towards said outlet opening.

3. A surgical implement as claimed in claim 1 wherein in the first said position, said piston is disposed at least partially between said side tube and said outlet opening.

4. A surgical implement as claimed in claim 3 wherein in said first position, said piston partially obstructs the mouth of said side tube.

5. A surgical implement as claimed in claim 1 wherein in the second said position, said piston is at least partially clear of said side tube.

6. A surgical implement as claimed in claim 1 wherein said barrel is provided with an internal abutment which is engageable by said piston to limit movement thereof in a direction away from said outlet opening.

7. A surgical implement as claimed in claim 1 wherein said piston is freely movable in said barrel in response to fluid flow.

8. A surgical implement for use as an irrigator/evacuator comprising double-acting manually operable pump means including a barrel in which an outlet opening is formed at one end through which fluid may be displaced outwardly and withdrawn inwardly, a side tube extending transversely from said barrel at a position near said outlet opening, reservoir means which comprises a vessel connected to said side tube, and a displaceable member arranged within said barrel for movement between a first position adjacent to said outlet opening and a second position spaced inwardly from said opening, the displaceable member comprising a piston which is moveable within said barrel with clearance and includes a transverse disc and radially arranged fins on one side of said disc remote from said outlet opening, said piston being so dimensioned and shaped as partially to obstruct said outlet opening when in said first position in order to restrain passage of pieces of tissue.

9. A surgical implement as claimed in claim 8 wherein said piston further includes an abutment member spaced from a side of said disc presented towards said outlet opening.

10. A surgical implement for use as an irrigator/evacuator comprising double-acting manually operable pump means including a barrel in which an outlet opening is formed at one end through which fluid may be displaced outwardly and withdrawn inwardly by the operation of the pump means, fluid reservoir means attached to and in fluid communication with the interior of said barrel, and a piston loosely received within said barrel but unattached thereto so as to move within said barrel between a first position adjacent said outlet opening and a second position spaced inwardly from said opening in response to fluid flow therein, said piston having a transverse disc and radially arranged fins on a side of said disc remote from the outlet opening and an abutment member spaced from said disc opposite the fins, and said piston being so dimensioned as to partially obstruct the passage of fluid thereby in order to restrain passage of materials entrained in a fluid, such as pieces of tissue.

* * * * *